(12) United States Patent
Heikkila et al.

(10) Patent No.: US 6,512,110 B1
(45) Date of Patent: *Jan. 28, 2003

(54) PROCESS FOR THE PRODUCTION OF XYLOSE FROM A PAPER-GRADE HARDWOOD PULP

(75) Inventors: Heikki Heikkila, Espoo (FI); Marja-Leena Sarkki, Kantvik (FI); Vili Ravanko, Kirkkonummi (FI); Mirja Lindroos, Kirkkonummi (FI)

(73) Assignee: Xyrofin Oy, Espoo (FI)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/456,902

(22) Filed: Dec. 8, 1999

Related U.S. Application Data

(63) Continuation of application No. PCT/FI98/00500, filed on Jun. 10, 1998.
(60) Provisional application No. 60/049,065, filed on Jun. 10, 1997.

(51) Int. Cl.[7] .............................. C07H 1/06; C12P 7/18
(52) U.S. Cl. .......................... 536/127; 127/37; 127/30; 127/42; 127/58; 435/105; 435/200; 435/158
(58) Field of Search ........................... 536/127; 127/37, 127/30, 42, 58; 435/105, 200, 158

(56) References Cited

U.S. PATENT DOCUMENTS

| | | | |
|---|---|---|---|
| 5,084,104 A | * 1/1992 | Heikkila et al. | 127/46.2 |
| 5,637,225 A | * 6/1997 | Heikkila et al. | 210/659 |
| 5,932,452 A | * 8/1999 | Mustranta et al. | 435/105 |
| 6,057,438 A | 2/2000 | Hyatt et al. | |
| 6,086,681 A | * 7/2000 | Lindroos et al. | 127/37 |

FOREIGN PATENT DOCUMENTS

| | | |
|---|---|---|
| EP | 0 159 795 A1 | 10/1985 |
| SE | 7811162 | 4/1979 |
| WO | WO 92/11376 | 7/1992 |
| WO | WO 92/11382 | 7/1992 |
| WO | WO 94/09144 | 4/1994 |
| WO | WO 94/11520 | 5/1994 |
| WO | WO 9602632 A1 | 2/1996 |
| WO | WO 9627028 * | 9/1996 |
| WO | WO 9816682 | 4/1998 |

OTHER PUBLICATIONS

Baecker et al., 1983, "Biosynthesis of bacterial glycogen. Primary structure of *Escherichia coli* 1,4–α–D–glucan:1, 4–α–D–glucan 6–α–D–(1,4–α–D–glucano)–transferase as deduced from the nucleotide sequence of the glgC gene", J. Biol. Chem. 258:5084–5088.

Bartels and Thompson, 1986, "Synthesis of mRNAs coding for abundant endosperm proteins during wheat grain development", Plant Sci. 46:117–125.

Bradford, 1976, "A rapid and sensitive method for the quantitation of microgram quantities of protein utilizing the principle of protein–dye binding", Anal. Biochem. 72:248–254.

Cheng et al., 1997, "Genetic transformation of wheat mediated by *Agrobacterium tumefaciens*", Plant Physiol. 115:971–980.

Clackson and Winter, 1989, ""Sticky–feet"–directed mutagenesis and its applications to swapping antibody domains", Nucl. Acids Res. 17:10163–10170.

Echt and Schwartz, 1981, "Evidence for the inclusion of controlling elements within the structural gene at the waxy locus in maize", Genetics 99:275–284.

Edwards et al., 1999, "A combined reduction in activity of starch synthases II and III of potato has novel effects on the starch of tubers", Plant J. 17:251–261.

Fromm et al., 1990, "Inheritance and expression of chimeric genes in the progeny of transgenic maize plants", Bio/Technology 8:833–839.

Gordon–Kamm et al., 1990, "Transformation of maize cells and regeneration fertile transgenic plants", Plant Cell 2:603–618.

Guerineau et al., 1988, "An expression cassette for targeting foreign proteins into chloroplasts", Nucl. Acids Res. 16:11380.

Keeling, 1997, "Plant biotechnology: technical barriers to starch improvement", Starch: Structure and Functionality 180–195, Eds. Frazier et al., Royal Society of Chemistry, Cambridge, UK.

Kiel et al., 1994, "Glycogen in *Bacillus subtilies*: molecular characterization of an operon encoding enzymes involved in glycogen biosynthesis and degradation", Mol. Microbiol. 11:203–218.

Korstee et al., 1997, "Characterization of starch from genetically modified potato after transformation with the bacterial branching enzyme of *anacystis nidulans*", in: *Starch: Structure and Functionality*, Frazier et al., eds., Royal Society of Chemistry, Cambridge, UK, pp. 238–247.

(List continued on next page.)

Primary Examiner—Samuel Barts
Assistant Examiner—Devesh Khare
(74) Attorney, Agent, or Firm—Scully, Scott, Murphy & Presser

(57) ABSTRACT

The invention relates to a process for the production of xylose from a paper-grade hardwood pulp comprising the steps of extracting xylan contained in said pulp into a liquid phase, subjecting the xylan contained in the obtained liquid phase to conditions sufficient to hydrolyze xylan to xylose, and recovering the xylose, wherein the extracting step includes at least one treatment of an aqueous suspension of said pulp or an alkali-soluble material thereof with a xylanase enzyme.

8 Claims, No Drawings

OTHER PUBLICATIONS

Kuipers et al., 1994, "Formation and deposition of amylose in the potato tuber starch granule are affected by the reduction of granule–bound starch synthase gene expression", Plant Cell 6:42–52.

Kumar et al., 1986, "Biosynthesis of bacterial glycogen. Primary structure of *Escherichia coli* ADP–glucose:α–1, 4–glucan, 4–glucosyltransferase as deduced from the nucleotide sequence of the glgA gene", J. Biol. Chem. 261:16256–16259.

Le Bail et al., 1997, "Structural and polymorphic transitions of amylose induced by water and ternperature changes", in: *Starch: Structure and Functionality*, Frazier et al., eds., Royal Society of Chemistry, Cambridge, UK, pp. 51–58.

Leung and Preiss, 1987, "Cloning of the ADPglucose pyrophosphorylase (*glgC*) with glycogen synthase (*glgA*) structural genes from *Salmonella typhimurium* LT2", J. Bacteriol. 169:4349–4354.

Raleigh et al., 1989, Current Protocols in Molecular Biology, Ausubel et al., eds., Wiley Interscience, New York, Unit 1.4.

Schägger and von Jagow, 1987, "Tricine–sodium dodecyl sulfate–polyacrylamide gel electrophoresis for the separation of proteins in the range from 1–100 kDa", Anal. Biochem. 166:368–379.

Shewmaker et al., 1994, "Expression of *Escherichia coli* glycogen synthase in the tubers of transgenic potatoes (*Solanum tuberosum*) results in a highly branched starch", Plant Physiol. 104:1159–1166.

Tester, 1997, "Starch: the polysaccharide fractions", in: *Starch: Structure and Functionality*, Frazier et al., eds., Royal Society of Chemistry, Cambridge, UK, pp. 163–171.

Uttaro and Ugalde, 1994, "A chromosomal cluster of genes encoding ADP–glucose synthetase, glycogen synthase and phosphoglucomutase in *Agrobacterium tumefaciens*", Gene 150:117–122.

Vasil et al., 1992, "Herbicide–resistant fertile transgenic wheat plants obtained by microprojectile bombardment of regenerable embryogenic callus", Bio/Technology 10:667–674.

Visser et al., 1991, "Expression of a chimaeric granule–bound starch synthase–GUS gene in transgenic potato plants", Plant Mol. Biol. 17:691–699.

Visser et al., 1991, "Inhibition of the expression of the gene for granule–bound starch synthase in potato by antisense constructs", Mol. Gen. Genet. 225:289–296.

\* cited by examiner

PROCESS FOR THE PRODUCTION OF XYLOSE FROM A PAPER-GRADE HARDWOOD PULP

This application is a continuation of application Ser. No. PCT/FI98/00500, filed on Jun. 10, 1998, and claims the benefit of provisional application No. 60/049,065, filed Jun. 10, 1997.

The present invention relates to a process for the production of xylose from a paper-grade, hardwood pulp. More specifically, this invention relates to a process wherein the xylan contained in said pulp is extracted using an aqueous solution of a xylanase enzyme. Optionally, the process also comprises one or two alkalic treatments. Xylose is obtained by a hydrolysis of the xylan exctracted from the pulp. The paper-grade hardwood pulp used as raw material is preferably soda pulp or kraft pulp. In one embodiment of the present invention, dissolving-grade pulp of high purity is co-produced with xylan.

Xylose is a valuable raw material in the sweets and flavouring industries, for example, and particularly as a starting material in the production of xylitol. Xylose is formed in the hydrolysis of xylan containing hemicellulose. Vegetable materials rich in xylan include wood material from wood species, particularly hardwood, such as birch, aspen and beech, various parts of grain (such as straw and husks, particularly corn and barley husks and corn cobs), bagasse, coconut shells, cottonseed skins, etc.

The dissolving-grade pulp obtained is useful in the manufacture of viscose rayon, cellulose esters such as cellulose acetate, cellulose acetate propionate and cellulose acetate butyrate. The production of these cellulose derivatives requires a source of high quality cellulose feedstock. Wood pulp, however, requires extensive purification before it is suitable for viscose or cellulose ester manufacture. The additional purification, which involves treatment with alkali to remove and destroy hemicelluloses and bleaching to remove and destroy lignin reduces the yield and increases the cost of "dissolving-grade" cellulose derived from wood pulp.

"Pulp" is an aggregation of random cellulosic fibers obtained from plant fibers. As used herein, the term "pulp" refers to the cellulosic raw material used in the production of paper, paperboard, fiberboard, and similar manufactured products. Pulp is obtained principally from wood which has been broken down by mechanical and/or chemical action into individual fibers. Pulp may be made from either hardwoods (angiosperms) or softwoods (conifers or gymnosperms). Hardwood and softwood pulps differ in both the amount and the chemical composition of the hemicelluloses which they contain. In hardwoods, the principal hemicellulose (25–35%) is glucuronoxylan while softwoods contain chiefly glucomannan (25–30%) (Douglas W. Reeve, Pulp and Paper Manufacture, Vol. 5, pp. 393–396).

There are three general types of chemical pulps:
(1) Soda pulp is produced by digesting wood chips at elevated temperatures with aqueous sodium carbonate.
(2) Kraft pulp is produced by digesting wood chips at temperatures above about 120° C. with a solution of sodium hydroxide and sodium sulfide. Some kraft pulping is also done in which the sodium sulfide is augmented by oxygen or anthraquinone. Although kraft pulping removes most of the lignin originally present in the wood, enough remains that a bleaching step is required to give pulp of acceptable color. As compared with soda pulping, kraft pulping is particularly useful for pulping of softwoods, which contain a higher percentage of lignin than do hardwoods.
(3) Sulfite pulp is produced by digesting wood with sulfur dioxide and an alkali such as calcium, magnesium, or sodium base. The process operates in the presence of a good deal of free sulfur dioxide, at low pH. Although this process, like kraft pulping, separates most of the lignin from the cellulose fibers, considerable color remains.

"Dissolving-grade pulp" is pulp which has been purified sufficiently for use in the production of viscose rayon, cellulose ethers, or cellulose esters with organic or inorganic acids. It may be produced from either kraft, soda, or sulfite pulp by bleaching and other treatments which will be discussed herein. Historically, dissolving-grade pulp (in contrast to paper-grade pulp) referred to pulp which reacted with carbon disulfide to afford a solution of cellulose xanthate which then could be spun into fibers (viscose rayon) with evolution of carbon disulfide and regeneration of cellulose. Dissolving-grade pulp now refers to pulp which is used to manufacture various cellulose derivatives such as inorganic and organic esters, ether, rayon and the like.

"Bleaching" is the removal of color from pulp, primarily the removal of traces of lignin which remains bound to the fiber after the primary pulping operation. Bleaching usually involves treatment with oxidizing agents, such as oxygen, peroxide, chlorine, or chlorine dioxide. Classically, the pulp is treated with chlorine, then extracted with caustic, and finally treated with hypochlorite. The alkaline extraction may be with either hot or cold caustic. The relative merits of extraction with cold, versus hot, caustic are discussed at length by M. Weyman in *The Bleaching of Pulp,* W. Howard Rapson, editor, *TAPPI Monograph Series* No. 27 (1963), Technical Association of the Pulp and Paper Industry, New York, N.Y., Chapter 5, pp. 67–103. Weyman concludes that cold caustic extraction is the superior method for xylan removal from pulp.

While the chief purpose of the chlorine and caustic treatments is to render the residual lignin in the pulp soluble and extractable, the caustic also degrades and dissolves not only a substantial amount of the hemicellulose, but it also attacks the cellulose itself, with resulting decreases in degree of polymerization and pulp yield. The low molecular weight of some of the hemicellulose fragments makes them hard to isolate, while in some cases (prehydrolysis kraft), the harsh conditions convert the hemicelluloses to decomposition products. In conventional operation, therefore, no attempt is made to recover useful products from the hemicellulose. Chlorine bleaches lead to undesired impurities and make recycle of caustic very difficult. The use of chlorine as the bleaching agent also inevitably produces traces of extremely toxic chlorinated dioxins.

One measure of the effectiveness of bleaching is the brightness of the resulting pulp. Brightness is defined as the reflectivity of a specified standard surface using blue light with a peak wavelength at 457 nm.

Hardwood pulp produced by the kraft process contains a significant amount of hemicelluloses, chiefly xylans. The xylans, in moderate amounts, are desirable in paper manufacture because they help maintain a random dispersion of fiber in the furnish, resulting in more uniform and mechanically stronger paper webs. However, when pulp is used in the production of cellulose esters and other cellulose derivatives, the pulp normally must contain a very low level of xylan. Hardwood kraft pulp for paper manufacture generally contains about 80 to 84% cellulose, about 15 to 20% xylans, and about 0.3–3% mannans. In contrast, dissolving-grade pulp suitable for cellulose ester manufacture for fiber and film applications should contain about 97 to 98.5 weight percent cellulose, not more than about 3 weight percent, e.g., 0.5 to 3 weight percent, xylans, and not more than about 0.5 weight percent, e.g., 0.1 to 0.5 weight percent, mannans. This requirement for higher purity necessitates more drastic treatment with alkali, with resulting decrease in pulp yield. Since the hemicelluloses removed normally are not recovered from such treatments, they are used, if at all, as fuel and have negligible value. The manufacture of dissolving pulps is discussed in detail by J. F. Hinck et al., Chapter VIII, Dissolving Pulp Manufacture in Volume 4, Sulfite Science & Technology of *Pulp and Paper Manufacture,* Third Edition, O. V. Ingruber, M. J. Kocurek, and A. Wong, ed., published by the Technical Section, Canadian Pulp and Paper Association Montreal, QC, Canada, pp. 213–243. Although the relative amounts of impurities vary somewhat between kraft and sulfite pulps, both contain significant amounts of lignin and hemicelluloses which must be reduced.

U.S. Pat. No. 4,008,285 (and related U.S. Pat. No. 4,075,406) contains a brief review of early attempts to produce xylose from natural products such as wood. The '285 patent also describes a process for purifying the pentosan-rich solution obtained by acid hydrolysis of xylan-containing raw material. The process involves first purifying the hydrolysate by ion exclusion and color removal, then subjecting the purified solution to chromatographic fractionation. The recovery of the pulp by-product is not disclosed.

U.S. Pat. No. 4,087,316 describes a process for removing cellulosic fibers from seed hulls, such as cottonseed, and for obtaining xylose by hydrolysis from the remaining hull fragments in the presence of dilute sulfuric acid. The resulting xylose hydrolysate may be hydrogenated to xylitol.

U.S. Pat. No. 4,742,814 discloses a process for obtaining xylitol and, optionally, cellulose and lignin from lignocellulose vegetable materials by treatment with a mixture of water and lower aliphatic alcohols and/or ketones at elevated temperature and pressure followed by separation of fibrous materials, organic solvents, and lignin from the treatment solutions. The oligosaccharides and polysaccharides remaining in solution from this process are hydrolyzed by dilute acid.

U.S. Pat. No. 5,084,104 is concerned with recovery of xylose from hydrolysates of such natural materials as birch wood, corn cobs, cotton seed hulls, etc. The disclosed process involves subjecting the hydrolysate to a chromatographic column comprising a strong anion exchange resin, and eluting a xylose-rich fraction. No reference is made to the recovery of any cellulose remaining after extraction of the xylose.

A more recent article (Gernot Gamerith and Hans Strutzenberger, *Xylans and Xylanases,* J. Visser et al., ed., (1992), pp. (339–348)) discusses the recovery of xylan during viscose pulp purification. Suggested uses are as a raw material for such products as furfural, xylitol, xylose, etc. In the process disclosed, beech-wood pulp produced by magnesium bisulfite cooking is first bleached with alkaline peroxide and hypochlorite, which reduces the xylan content to about 3.6%. This pulp is then treated with "high concentrated" sodium hydroxide solution to reduce the xylan content sufficiently for the pulp to be used in viscose production. Xylan is recovered by acidification of the caustic solution. An unspecified amount of xylan remains in the final pulp which, apparently, is sufficiently pure for use in viscose rayon production. Although no pulp yields are given, the rather drastic alkali treatment suggests that the process resulted in a substantial loss of cellulose.

Bleaching is another step in pulp production. Conventional bleaching processes involving chlorine and alkali present environmental problems as mentioned above, and they also substantially reduce the amount of dissolving-grade pulp which can be recovered from wood. Some work has been done to determine whether the xylans in wood pulp can be hydrolyzed and removed by the action of enzymes. Most prior work has been concerned merely with sufficient removal of xylan to free residual lignin which is bound to the fibers, and aid in pulp bleaching. A number of articles and reviews have been published which deal with this aspect of the use of enzymes in pulping. A review, Enzymatic Treatment of Pulps by Thomas W. Jeffries in *Emerging Technologies for Materials and Chemicals from Biomass,* Roger M. Rowell, Tor P. Schulz, and Ramani Narayan, ed.; *Advances in Chemistry Series* No. 476 (1992), pp. 322–327 discusses pulp bleaching with hemicellulases. A recent article (L. P. Christov and B. A. Prior, *Enzyme and Microbial Technology,* 18, 244–250 (1996)) describes the use of repeated, alternating, treatments with the hemicellulases derived from the yeast, Aureobasidium pullulans and alkali to enchance bleaching of sulfite pulps. The production of xylose is not discussed in these articles.

The following U.S. patents disclose the use of enzymes as an aid in pulp bleaching. None of these patents discloses the production and/or recovery of chemical-grade, or dissolving-grade pulp, and none discusses the recovery of xylose.

U.S. Pat. No. 5,457,046 discloses enzymes with xylanolytic activity.

U.S. Pat. No. 5,407.827 discloses pulp bleaching by means of delignification using thermostable xylanase.

U.S. Pat. No. 5,395,765 discloses a process for treating pulp with an enzyme to improve pulp bleachability and reduce the amount of chlorine used.

U.S. Pat. No. 5,369,024 discloses the use of xylanase for removing color from kraft wood pulps.

U.S. Pat. No. 5,179,021 discloses a pulp bleaching process comprising oxygen delignification and xylanase enzyme treatment.

U.S. Pat. No. 5,116,746 discloses that cellulase-free endoxylanase enzyme is useful in pulp delignification.

U.S. Pat. No. 5,081,027 discloses a method for producing pulp by a treatment using a microorganism and its related enzymes.

U.S. Pat. No. 2,280,307 discloses a process of manufacturing paper.

Finnish Patent 55,516 discloses a method for the production of xylan from bleached or unbleached kraftwood pulp. According to said method, the pulp is treated with aqueous alkali, and xylan is precipitated from the alkalic solution by carbon dioxide. Xylan with a high purity—and therefore suitable for the production of xylose—is said to be obtained. The xylan yields based on the xylan contained in the starting pulp are not discussed.

The mechanism by which hemicellulose-degrading enzymes (xylanases and mannanases) assist in color removal or brightening of wood pulp is not completely clear and may be complex (Saake, Clark, & Puls, *Holzforschung,* 49, pp. 60–68 (1995)). Internal structural changes in the pulp fibers, in addition to surface modification by hydrolysis of reprecipitated xylan from the surface of kraft fibers and loosing of the bonds between the hemicelluloses and residual lignin may also be important.

Christov and Prior, *Biotechnology Letters* 13, 1269–1274 (1993) describe the preparation of dissolving pulp, in contrast to paper-grade pulp, by treating bleached sulfite (not kraft) pulp with xylanases, specifically enzymes of *Aureobasidium pullulans.* They state that even with high enzyme loadings and 24 hour incubation periods, xylan removal was limited. The use of xylanases in pre-bleaching of bamboo kraft pulp for paper manufacture recently has been reported (Pratima Bajpai and Pramod K. Bajpai, *TAPPI Journal* 79(4), 225.230 (1996)).

We have found that an enzymatic treatment according to the invention improves the quality of the pulp for use as a source of xylan in that it improves the solubility of xylan whereby xylan is more easily removed from pulp. This results in increased recovery of xylan and, accordingly, higher yields of xylose. Without being bound to the theory, these improvements are believed to have their basis in the increased solubility of xylan, which is caused by the xylanase treatment.

Accordingly, an object of the present invention is to provide a process for the production of xylose from a paper-grade hardwood pulp comprising the steps of:

extracting xylan contained in said pulp into a liquid phase;

subjecting the xylan contained in the obtained liquid phase to conditions sufficient to hydrolyze xylan to xylose; and recovering the xylose, wherein the extracting step includes at least one treatment of an aqueous suspension of said pulp or an alkali-insoluble solid material thereof with a xylanase enzyme.

In this specification and appended claims, the term "xylan" refers both to the native xylans present in the paper-grade hardwood pulp and to the slightly degraded products formed from these native xylans during the xylanase treatment of the present invention.

In one embodiment of the invention, the process comprises a treatment of the pulp with an aqueous solution of an alkali before the xylanase treatment. According to this embodiment, the solid material separated from the alkali slurry is subjected to a xylanase treatment.

In another embodiment, the process of the invention comprises, instead of or in addition to the above alkalic treatment, an alkalic treatment of the solid material obtained from the liquid/solid separation after the xylanase treatment.

In the process of the present invention, either the starting pulp or the solid material obtained after the alkalic treatment of the pulp is contacted with a mixture of water and an effective amount of at least one xylanase enzyme.

In a preferred embodiment, the process of the present invention further comprises an alkalic treatment of the pulp and/or of the solid material obtained from said liquid/solid separation. Especially, the process containing an alkalic treatment both before and after the xylanase treatment results in a simultaneous production of dissolving-grade pulp of very high quality and high yields of xylose.

The xylanase enzymes preferably used in the practice of the present invention are those xylanase enzymes which are substantially free of cellulase activity, i.e., those which do not substantially degrade the cellulose content of the pulp. See, for example, the xylanase enzymes described in U.S. Pat. Nos. 5,369,024, 5,395,765 and 5,407,827 and the references disclosed in these patents. In the preferred embodiment of the present invention, which contains an alkalic treatment both before and after the xylanase treatment, such xylanase enzymes afford a cellulose product with a sufficiently low xylan content. Suitable xylanases are available from a number of sources and exhibit a wide range of activities under a variety of operating conditions. The variability of enzymes and the optimum conditions at which they are effective is further discussed by Bajpai and Bajbai, *TAPPI Journal* 79(4), 225–330 (1996).

In general, the enzyme treatment is carried out at a temperature between about 0 and 80° C., preferably between about 20 and 80° C., and most preferably between 30° C. and 70 ° C., at a pH between 2 and 12 for a time between 0.1 and 10 hours, preferably between 0.5 and 3 hours. The pH and temperature at which an enzyme exhibits maximum activity vary substantially and are highly specific for a given enzyme. The pH and temperature at which a given enzyme is most effective can be determined readily by those skilled in the art.

The amount of xylanase enzyme required to give satisfactory results depends upon the degree of xylan removal which is desired, the reaction conditions, and the particular enzyme used. Although xylanase assay typically is expressed by enzyme manufacturers as "units/mL", the units are measured differently by different manufacturers and, consequently, the "units/mL" assay is meaningful, if at all, only with respect to a specific enzyme supplied by a specific manufacturer. For a given enzyme type and source, the amount of enzyme to be used is that required to give the desired purity of dissolving grade pulp. The weight ratio of water to the solid pulp material (dry basis) during the xylanase treatment may be about 2:1 to 1000:1, preferably about 4:1 to 35:1.

The slurry obtained after the xylanase treatment is subjected to conventional liquid/solid separation wherein the solid material present in the slurry is separated, e.g. by filtration or centrifugation, from the liquid phase comprising a solution of xylanase enzyme, xylan and water.

In the alkalic treatments optionally included in the process of the present invention, the solid pulp material to be treated is contacted or digested with an aqueous sodium hydroxide solution at a temperature of about 50 to 100° C. Said solid pulp material may be the paper-grade hardwood pulp used as the raw material or the solid material obtained after the xylanase treatment. It is an important element of this embodiment of the present invention that the entire extraction/maceration is performed at a temperature in the range of 50 to 100° C. The concentration of the sodium hydroxide in the aqueous sodium hydroxide solution normally is about 8 to 12 weight percent, with a concentration of about 9 to 10 weight percent being preferred. The amount of paper-grade pulp typically present in the pulp/aqueous sodium hydroxide slurry is in the range of about 3 to 15, preferably about 7 to 10 weight percent based on the total weight of the slurry. A particularly unique feature of the present invention is the use of elevated temperatures, e.g. about 50 to 100° C. during the aqueous caustic treatment. It is preferred to carry out the caustic treatment at a temperature of about 60 to 80° C. The time required for the treatment can vary substantially depending on various factors, such as the particular pulp, sodium hydroxide concentration and temperature employed. Contact times of about 1 to 30 hours are typical although contact times in the range of about 0.1 to 1 hour normally are adequate.

The slurry obtained from the above alkalic treatment is subjected to a conventional liquid/solid separation wherein the solid material present in the slurry is separated, e.g., by filtration or centrifugation, from the liquid phase comprising a solution of sodium hydroxide, xylan and water. Residual sodium hydroxide present in the solid material is reduced or removed by washing the material with water. Normally, the material is washed, for example, either by washing the filter cake on the filter, by counter current washing or by reslurrying the solids collected in water, until the wash water has a pH of less than about 8, preferably a pH in the range of about 6 to 8. This liquid/solid separation is preferably carried out at a temperature of about 50 to 100° C., most preferably about 60 to 80° C. This preferred embodiment results in a co-production of dissolving-grade pulp which contains little, if any, cellulose II and, therefore, is especially useful for use in the manufacture of carboxylic acid esters of cellulose.

Xylan is recovered from the liquid phase obtained after the xylanase treatment or, in the case that an alkalic treatment follows the enzymatic treatment, from any of the liquid phases obtained after these two treatments or from a combination of these liquid phases, by known procedures. A preferred method for recovering the xylan comprises the alcohol precipitation procedure described in U.S. Pat. No. 3,935,022. In this method, one or more $C_1$–$C_4$ alkanols are combined with the liquid phase to precipitate the xylan from the liquid. Thus, the liquid phase is preferably combined with one or more $C_1$–$C_4$ alkanols to effect precipitation of xylan from the liquid and the resulting mixture is subjected to liquid/solid separation to recover xylan. The volume of the alkanol(s) combined with the liquid of said steps to effect xylan precipitation may be in the range of about 50 to 200% of the volume of the liquid although alkanol volumes of about 80 to 120% (same basis) are more typical. Methanol and ethanol are particularly preferred alkanols. The liquid may be concentrated, e.g. by vaporization or membrane separation procedures, prior to being combined with the alkanol(s).

The alkanol-containing solution obtained from the separation of precipitated xylan may be subjected to distillation to recover the alkanol(s), and in the case that NaOH is present in said solution, also the aqueous sodium hydroxide. Thus, both the alkanol(s) and the aqueous sodium hydroxide may be used repeatedly in the process.

Alternatively, a liquid phase obtained after the xylanase treatment and subsequent alkalic treatment can be concentrated by removal of water by distillation of multiple-effect evaporation until the concentration of sodium hydroxide is about 40–50 weight percent. This concentrated solution can be treated with a $C_1$–$C_4$ alkanol to precipitate the xylan. About 1 volume equivalent of alkanol is required. The precipitated xylan is recovered by filtration, centrifugation, or the like, and the filtrate distilled to recover the alkanol and leave a concentrated sodium hydroxide solution which can be diluted to the desired concentration for use in the xylan extraction process.

In another variation, said liquid phase can be subjected to nanofiltration through a caustic-stable membrane which allows passage of water and sodium hydroxide but does not allow the passage of dissolved organic compounds having a molecular weight above a few hundred, e.g. xylan. This process variation produces a clean sodium hydroxide stream ready for re-use and a much smaller stream in which the xylan is highly concentrated in aqueous sodium hydroxide. The xylan in this organic-rich stream may be recovered by alkanol precipitation as described above, or by neutralization of the sodium hydroxide by the addition of a mineral acid which also precipitates the xylan.

The xylan recovered as described above is converted to xylose according to conventional procedures, e.g. by acid hydrolysis or enzymatically. Procedures for the conversion of xylan to xylose and further to xylitol, and recovery processes, are described in more detail in U.S. Pat. Nos. 4,008,356, 4,025,356, 4,075,406 and 5,084,104. An acid hydrolysis suitable for converting xylan to xylose is disclosed, for instance, in WO publication No. 96/27028.

For example, heating a slurry of xylan in water, e.g. a slurry containing from about 5 to 25 weight percent solids, in the presence of a mineral acid produces xylose. The heating is normally effected at a temperature in the range of about 70 to 150° C., preferably at about 90 to 120° C. Examples of suitable mineral acids include sulfuric acid, hydrochloric acid and phosphoric acid.

An enzymatic conversion of xylan to xylose can be carried out, e.g. by following the procedures described in WO publication No. 91/03566 and the litterature sources referred to therein.

Xylose can be recovered from the obtained xylan hydrolysate by known procedures. The hydrolysate may first be purified, for instance, using chromatographic methods. If acid hydrolysis is used for the conversion of xylan to xylose, the excess of anions can be removed from the hydrolysate, e.g. by precipitation. As a last step, xylose may be recovered from the hydrolysate or a purified solution obtained from it by crystallization using known methods, e.g. as disclosed in WO publication No. 96/27028.

The processes of the present invention are further illustrated by the following examples. The analysis results given in the examples have been obtained by the following methods:

In Examples illustrating the conversion of xylan to xylose, the dry solids contents were determined by the Karl Fisher titration method (DS) or by the refractive method (RDS).

Carbohydrates were analyzed by liquid chromatography (HPLC) employing columns in which the ion exchange resin was in $Pb^{2+}$ form, or with PEDLC (i.e. HPLC employing a pulse electrochemical detector). The acetic acid content was analyzed with HPLC (the ion exchange resin in the column was in the $H^+$ form), the sulfate content by ion chromatography and the calcium content with ICP (Inductively Coupled Plasma Spectrophotometry). The oligosaccharides referred to in the test results also include the disaccharides.

EXAMPLES 1–7

These examples illustrate of treatment of aspen papergrade kraft pulp with 10 weight percent aqueous sodium hydroxide and relatively low levels of a xylanase enzyme available under the name Irgazyme 10A-X4 (4400 units of enzyme per ml, Genencor International, Inc.). The papergrade pulp had a Cuene IV of 7.97 and contained 17.80 weight percent xylan and 0.33 weight percent mannan.

The paper-grade pulp (10 g) was shredded into approximately 1 inch×3 inch (2.54 cm×7.62 cm) pieces and mixed with 200 ml of a 10 weight percent solution of sodium hydroxide in deionized water. The pulp and caustic were mixed thoroughly and shaken at different temperatures for different periods of time. The pulp was then transferred to a porous cloth bag and washed under running deionized water for 1 hour.

The bag containing the pulp was squeezed to remove excess water, then the pulp was added to 200 ml of deionized water, the pH of which had been adjusted to pH 4.5 by addition of sodium acetate if required, and which contained the enzyme. The slurry was mixed well, and placed in a constant temperature shaker bath at 30° C. for 1 hour. The mixture was transferred to a wash bag and washed as before for 1 hour.

The solid material resulting from the enzyme treatment was treated with aqueous sodium hydroxide and washed using the same sodium hydroxide concentration, treatment time and temperature used in the first aqueous sodium hydroxide treatment. After the second aqueous sodium hydroxide treatment and wash, the pulp was removed from the wash bag and placed in a temperature controlled oven overnight or until dry. Samples of the dissolving-grade pulp thus obtained were analyzed for Cuene IV and for sugars by acidic digestion to monomers followed by liquid chromatography. The conditions used in the aqueous sodium hydroxide exctractions and the results achieved are shown in Table I wherein "Time" is period of time (minutes) and "Temp" is the temperature (°C) of each aqueous sodium hydroxide treatment; "Enzyme Conc" is the units of xylanase enzyme present during the enzyme treatment per g of paper-grade pulp used initially; "Cuene IV" has the meaning given above; and the values given under "Xylose" and "Mannose" are the weight percentages of xylose and mannose, respectively, present in the dissolving grade pulp obtained in each example. The comparative examples are characterized as C-1, C-2, etc.

The results set forth in Table I clearly show that the sequential caustic/enzyme/caustic treatments are effective to purify paper-grade pulp and convert it to dissolving-grade pulp and that the caustic treatments at 70° C. are more effective than 30° C.

TABLE I

| Example | Time | Temp | Enzyme Conc | Cuene IV | Xylose | Mannose |
|---|---|---|---|---|---|---|
| C-1 | 30 | 30 | 20 | 7.92 | 2.68 | 0.67 |
| C-2 | 60 | 30 | 20 | 7.55 | 2.60 | 0.72 |
| C-3 | 60 | 30 | 60 | 6.14 | 2.40 | 0.65 |
| C-4 | 30 | 30 | 60 | 6.52 | 2.73 | 0.62 |
| 1 | 60 | 70 | 60 | 5.93 | 1.85 | 0.75 |
| 2 | 45 | 50 | 40 | 6.95 | 2.15 | 0.70 |
| 3 | 30 | 70 | 20 | 7.21 | 2.32 | 0.68 |
| 4 | 45 | 50 | 40 | 6.33 | 2.30 | 0.63 |
| 5 | 30 | 70 | 60 | 6.46 | 2.23 | 0.66 |
| 6 | 60 | 70 | 20 | 6.22 | 2.13 | 0.68 |
| 7 | 45 | 50 | 40 | 6.63 | 2.57 | 0.62 |

EXAMPLES 8 and 9 and

Comparative Examples 5 and 6

The general procedure described in Examples 1–7 was repeated for Examples 8–11 and Comparative Examples 5–8 using the same paper-grade pulp. The enzyme concentration used in the xylanase enzyme treatment step was 40 units of Irgazyme 10A-X9 xylanase enzyme per g of paper-grade pulp used initially in each example. The enzyme treatment step was carried out at pH 4.5 and 30° C. The consistency used in these examples was 4.76 wherein "consistency" refers to the g of paper-grade pulp initially used per g reaction mixture, expressed as a percentage, during the enzyme treatment step. The conditions used in the aqueous sodium hydroxide extractions and the results achieved are shown in Table II wherein "Time", Temp", "Cuene IV", "Xylose" and "Mannose" have the meanings given above for Table I. Since the pulp lost some weight as soluble xylan and since it was charged as a wet solid without compensating for the diluting effect of the water, the actual sodium hydroxide concentration and consistency were somewhat lower in the second sodium hydroxide extraction than in the first.

TABLE II

| Example | Time | Temp | Cuene IV | Xylose | Mannose |
|---|---|---|---|---|---|
| C-5 | 30 | 30 | 7.66 | 5.31 | 0.70 |
| 8 | 30 | 70 | 7.51 | 2.00 | 0.47 |

TABLE II-continued

| Example | Time | Temp | Cuene IV | Xylose | Mannose |
|---|---|---|---|---|---|
| C-6 | 60 | 30 | 8.15 | 2.98 | 0.50 |
| 9 | 60 | 70 | 7.61 | 1.73 | 0.76 |

The data presented in Table II clearly show that the lowest xylose content is reached when the caustic treatments are carried out at 70° C. for 60 minutes. Although Comparative Example C-6 shows that a caustic extraction temperature of 30° C. can produce a pulp having less than 3 weight percent xylan, in all cases the use of 70° C. gives superior results when other variables are the same. We have found that, in general, higher concentrations of sodium hydroxide give better results with a concentration of about 10 weight percent being the best.

EXAMPLES 10 and 11 and

Comparative Examples 7–12

Examples 10 and 11 and Comparative Examples 7–12 show the effect of varying the sequence of the aqueous sodium hydroxide treatments (designated "E") and the xylanase enzyme treatment(s) (designated "X") on the xylan content of treated pulp using two different enzymes: Irgazyme 40-X4 xylanase in Examples 10 and Comparative Examples 7–9 and Buzyme xylanase (available from Buckman Laboratories) in Example 11 and Comparative Examples 10–12. In these examples, each aqueous sodium hydroxide treatment was carried out at 70° C. with 10 weight percent aqueous sodium hydroxide using the general procedure and the paper-grade pulp described in Examples 1–7. In Example 10 and Comparative Examples 7–9 the concentration of the enzyme was 20 units of xylanase enzyme per g of pulp, the pH of the enzyme step was 6.5 and the temperature of the enzyme step was 30° C. In Example 11 and Comparative Examples 10–12 the concentration of the enzyme was 60 units of xylanase enzyme per g of pulp, the pH of the enzyme step was 7.0 and the temperature of the enzyme step was 70° C. The sequence of treatments used and the results achieved in each example are shown in Table III wherein the letters set forth below "Treatment Sequence" identify the order (proceeding from left to right) of the treatments carried out in each example and "Cuene IV", "Xylose" and "Mannose" have the meanings given above for Table I. The values given for "Weight Yield" are determined by:

TABLE III $$\% \text{ Yield} = \frac{\text{Dry Weight of Treated Pulp}}{\text{Dry Weight of Paper-Grade Pulp}} \times 100$$

| Example | Treatment Sequence | Cuene IV | Xylose | Mannose | Weight Yield |
|---|---|---|---|---|---|
| C-7 | X-E-E | 7.45 | 2.52 | 0.61 | 76 |
| C-8 | X-E-X | 6.61 | 3.14 | 0.68 | 77 |
| 10 | E-X-E | 7.67 | 1.63 | 0.81 | 75 |
| C-9 | E-E-X | 5.76 | 2.21 | 0.69 | 75 |
| C-10 | X-E-E | 6.34 | 2.35 | 0.69 | 75 |

TABLE III-continued $$\% \text{ Yield} = \frac{\text{Dry Weight of Treated Pulp}}{\text{Dry Weight of Paper-Grade Pulp}} \times 100$$

| Example | Treatment Sequence | Cuene IV | Xylose | Mannose | Weight Yield |
|---|---|---|---|---|---|
| C-11 | X-E-X | 7.43 | 3.01 | 0.72 | 77 |
| 11 | E-X-E | 7.98 | 1.28 | 0.70 | 75 |
| C-12 | E-E-X | 6.91 | 1.99 | 0.68 | 76 |

EXAMPLES 12–15 and

Comparative Examples 13–18

The general procedure described in Examples 1–7 was repeated for Examples 12–15 and Comparative Examples 13–18 using a eucalyptus, kraft, paper-grade pulp having a Cuene IV of 6.09, a xylan content of 14.49 weight percent and a mannan content of 0.55 weight percent. The xylanase enzyme (Irgazyme 40-X4) treatment was carried out at pH of 6.5 using a sodium acetate/acetic acid buffer, at 30° C. for 60 minutes. The enzyme concentration used in the enzyme treatment step was varied from 0 to 50 units of xylanase enzyme per g of paper-grade pulp used initially. In the examples in which no enzyme was used, the pulp was treated with an aqueous buffer solution at pH 6.5 for 30° C. for 60 minutes. Each aqueous sodium hydroxide extraction was carried out for 60 minutes using 10 weight percent aqueous sodium hydroxide solution and the temperatures shown in Table IV. The temperatures used in the first and second aqueous sodium hydroxide extractions ("First Caustic" and "Second Caustic") and the results achieved are shown in Table IV wherein "Enzyme Conc", "Cuene IV", Xylose" and "Mannose" have the meanings given above for Table I.

TABLE IV

| Example | First Caustic | Second Caustic | Enzyme Conc | Cuene IV | Xylose | Mannose |
|---|---|---|---|---|---|---|
| C-13 | 30 | 30 | 0 | 6.30 | 5.09 | 0.38 |
| C-14 | 70 | 30 | 0 | 6.53 | 3.34 | 0.33 |
| 12 | 70 | 70 | 50 | 4.89 | 2.26 | 0.39 |
| 13 | 50 | 50 | 25 | 5.06 | 2.56 | 0.34 |
| C-15 | 70 | 30 | 50 | 5.72 | 2.33 | 0.32 |
| C-16 | 30 | 70 | 0 | 4.95 | 2.64 | 0.26 |
| 14 | 50 | 50 | 25 | 5.95 | 2.74 | 0.33 |
| C-17 | 30 | 70 | 50 | 5.69 | 2.96 | 0.25 |
| C-18 | 70 | 70 | 0 | 5.49 | 3.19 | 0.36 |
| 15 | 50 | 50 | 25 | 5.38 | 2.73 | 0.27 |

EXAMPLE 16

Aspen paper-grade kraft pulp (20 g) similar to that used in Example 1 was preheated to about 70° C. To the pulp was added a volume of 10 weight percent aqueous sodium hydroxide, preheated to 70° C., sufficient to give a suspension of 7 weight percent pulp in the aqueous sodium hydroxide. The mixture was maintained at 70° C. for 1 hour, filtered hot, (200 ml of filtrate was recovered and set aside for xylan recovery) and the pulp washed with 70° C. water until the filtrate was at pH 7. The pulp was then diluted to 7 weight percent concentration with distilled water, and 0.166 ml of a commercial xylanase (6000 units/ml) was added to the slurry. This mixture was maintained at 70° C. for 1 hour. The pulp again was separated by filtration and combined with sufficient 10 weight percent aqueous sodium hydroxide to give a 7 weight percent pulp suspension. After 1 hour at 70° C., the pulp was filtered hot, washed with 70° C. water until the filtrate was neutral, and then dried in a 45° C. forced-air oven. The dried pulp weighed 16.1 g and contained 2.53 weight percent xylose.

The 200 ml of the xylan-containing, aqueous sodium hydroxide filtrate obtained above was stripped to approximately 100 ml and combined with 100 ml methanol to precipitate the xylan which was collected by filtration. The solid xylan was washed with water and ethanol, and then dried to give 2.1 grams of xylan product.

EXAMPLE 17

This example illustrates the utility of xylan as an intermediate for the preparation of xylose. A mixture of 50 g of water wet xylan (equivalent to 7.75 g dry xylan) isolated from paper-grade aspen pulp according to the process of the invention was mixed with 100 ml water and 3 ml sulfuric acid. After being stirred overnight at reflux, the initial slurry became a dark solution. The mix was cooled, neutralized by addition of sodium acetate, treated with a small amount of decolorizing charcoal, filtered, and freeze-dried to give 12 g of crude product comprising xylose, sodium sulfate and sodium acetate. Analysis by HPLC indicated the presence of 51.7 weight percent xylose (70.4% of theory) and 0.6% xylobiose.

EXAMPLE 18

A) Preparation of hydrolysate

The raw material was aspen xylan isolated from sulfate pulp by the process of the present invention. The composition of the xylan was as follows (percentages calculated on dry solids):

| | |
|---|---|
| Dry solids content | 21.1 g/100 g |
| Carbohydrates after hydrolysis: | |
| oligosaccharides | 0.8% |
| glucose | 0.4% |
| xylose | 91.4% |
| galactose + rhamnose | 0.0% |
| arabinose | 0.7% |
| mannose | 0.6% |

The preparation of the hydrolysate was carried out in a container equipped with effective mixing means and a heat exchanger (coil) for heating and cooling. 38 kg of the xylan, i.e. 8.0 kg DS, and 85 l of ion exchange water were mixed at about 45° C. to make a homogenous mixture. The mixture was heated to 95° C. 4500 ml of 48 w/v-% sulfuric acid was dosed into the mixture, and mixing was continued at 95° C. for 18 hours. Thereafter, the mixture (i.e. hydrolysate) was cooled to 45° C. (cooling time about 1 h). The hydrolysate was filtered with a Seitz Pilot filter using 250 g of diatomaceous earth (Kenite 300) as a body feed and a cake thickness of 0.5–1 cm. The filtrate was concentrated with Luwa evaporator to DS of 33.5 g/100 g.

The composition of the concentrated hydrolysate was (percentages calculated on dry solids):

| | |
|---|---|
| Dry solids content (DS) | 33.5 g/100 g |
| pH | 0.5 |
| Carbohydrates: | |
| oligosaccharides | 1.1% |
| glucose | 0.5% |
| xylose | 70.6% |
| galactose + rhamnose | 0.0% |
| arabinose | 0.0% |
| mannose | 0.2% |
| Acetic acid | <0.1% |
| Sulfate | 19.1% |

B) Chromatographic separation of aspen xylan hydrolysate

The aspen xylan hydrolysate obtained in step A above was separated into three fractions by a chromatographic separation in a pilot chromatographic column in order to separate sulfate ions and xylose from the hydrolysate. The chromatographic system consisted of a column, a feed pump, a heat exchanger, an outlet pump, a flow control device and pipelines for inlets and outlets of the feed liquor and eluent water.

The column having a diameter of 0.225 m was filled with a cation exchange resin (Finex CS 13 GC). The resin was a polystyrene matrix containing divinylbenzene as a crosslinking substance. The mean particle size and the crosslinking degree of the resin were 0.38 mm and 6.5%, respectively. The bed height of the resin in the column was 4.8 m. The resin was regenerated into hydrogen ($H^+$) form. The temperature of the column and the introduced feed liquor was about 60° C. The flow rate in the column was 20 liters/h.

The feed solution was evaporated and filtered by using a pressure filter and diatomaceous earth as a filter aid as described above in step A before separation. The separation was carried out as follows.

Step 1: Dry substance of a feed solution was adjusted to about 30 g dry substance in 100 g solution; the dry substance content was determined by the refractive method.

Step 2: 3.85 kg dry substance in the feed solution was fed to the top of the column.

Step 3: The feed line was washed with water in order to feed all of the feed solution into the column.

Step 4: The feed was eluted downwards in the column by feeding pure ion exchanged water to the top of the column.

Step 5: The conductivity and density of the outcoming solution were measured continuously and recorded. On the basis of the data received, the outcoming solution was collected and divided into three fractions: a salt fraction containing e.g. sulfate ions, a recycle fraction containing a small amount of salts and xylose, and a xylose fraction.

The composition of the feed solution and the three fractions is shown in Table V.

TABLE V

| | RDS g/100 g | xylose % on DS | $SO_4^{2-}$ % on DS | xylobiose % on DS |
|---|---|---|---|---|
| Feed solution | 31.5 | 71.8 | 20.3 | — |
| Salt fraction | 2.3 | 0 | 97.7 | 4 |
| Recycle fraction | 2.3 | 24.4 | 4.5 | 4.7 |
| Xylose fraction | 12.3 | 88.7 | 0.06 | 0.6 |

C) Crystallization after chromatographic separation

The xylose fraction(s) obtained from the chromatographic separation above was concentrated with a Luwa evaporator to a dry solids content (DS) of 65 g/100 g. Concentration was continued with an evaporator (Buchi Rotavapor R-151) to a refractometric dry solids content (RDS) of 80.1 g/100 g. 6.3 kg of the concentrated mass was transferred into a 6 l cooling crystallizer at a temperature of 70° C. The mass was seeded with 2.5 g of xylose powder (made by Xyrofin Ltd., grain size 15 µm). After about one hour, a linear cooling program from 70° C. to 30° C. during 60 hours was started.

During cooling, the bath temperature, i.e. temperature of the jacket of the crystallizer, and the refractive index of the mother liquid were monitored.

After cooling, the mass was mixed at 30° C. for about 7 hours before the crystals were separated by centrifuging (Hettich Roto Silenta II centrifuge, basket diameter 24 cm) for five minutes at 3500 rpm. The crystal cake was then washed with distilled water.

The results are shown in Table VI below, in which the terms have the following meanings:

Cake=crystal cake washed with water

Run-off=run-off from the centrifuging

Yield DS/DS=percentage of cake dry solids on dry solids of crystallization mass.

Purity=xylose purity, i.e. the proportion of xylose in dry solids.

TABLE VI

| Results of centrifugation. | |
|---|---|
| Mass to the centrifuge (g) | 796 |
| DS of mass (w-%) | 79.1 |
| Purity of mass (% on DS) | 79.3 |
| Crystal cake (g) | 251 |
| DS of cake (w-%) | 97.0 |
| Purity of cake (% on DS) | 96.2 |
| Purity of run-off (% on DS) | 63.9 |
| Yield in centrifugation, DS/DS (w-%) | 39 |

EXAMPLE 19

5990 g of the hydrolysate obtained in step A of Example 18 above was mixed with milk lime in a reaction vessel having a jacket, at 60° C. The amount of $Ca(OH)_2$ in the lime was 293.7 g, which was equal to the molar amount of sulfate ions in the hydrolysate. Stirring was continued at 60° C. for 1 hour. The solution was then filtered through glass fiber filter paper.

The analysis results of the filtrate after sulfate precipitation are shown in Table VII.

TABLE VII

| | |
|---|---|
| Dry solids content (DS) | 19.3 g/100 g |
| Sulfate content | 0.21 g/100 g |
| Carbohydrate content, % on dry solids | |
| glucose | 0.8% |
| xylose | 81.9% |
| galactose + rhamnose | 0.1% |
| arabinose + mannose | 1.4% |

Before starting the xylose crystallization, the filtrate obtained above was filtered through a diatomaceous earth cake (Kenite 300) with a thickness of about 1 cm. 5350 g of the filtrate thus obtained, having RDS of 19.9 g/100 g, was evaporated in a rotating evaporator (Büchi Rotavapor R-151) to RDS of 82.3 g/100 g. The mass was transferred into a 2 l vertical reaction vessel with a jacket at a temperature of 70° C., and the mass was stirred with an anchor mixer blade. The mass was cooled from 70° C. to 32° C. during 89 hours. The mass was stirred at the end temperature of 32° C. for about 3 hours before the mass was centrifuged (Hettich Roto Silenta II centrifuge, basket diameter 24 cm) at 2500 rpm for 5 min.

The results of the centrifuging test are shown in Table VIII below, in which the terms have the same meanings as in Example 18.

TABLE VIII

| | |
|---|---|
| Mass to the centrifuge (g) | 422 |
| DS of mass (w-%) | 83.7 |
| Purity of mass (% on DS) | 80.2 |
| Crystal cake, (g) | 182 |
| DS of cake (w-%) | 98.8 |
| Purity of cake (% on DS) | 93.0 |
| Purity of run-off (% on DS) | 63.5 |
| Yield in centrifugation, DS/DS (w-%) | 51 |

EXAMPLE 20

Aspen xylan extracted with sodium hydroxide from the aspen pulp was hydrolyzed with xylanase enzymes (produced by Genencor International) to xylose. The enzymes have xylanase and beta-xylosidase activities, which are essential properties to degrade xylan to xylose. Hydrolysis experiments with various enzyme dosages were carried out for 22 and 45 hours at pH of 4.5 to 5 at a temperature of 45° C. by stirring in a shaking water bath. The dry solids content in the hydrolysis was 50 g/l. After hydrolysis, the samples were boiled for 2 min before analysis. The total amount of solubilized carbohydrates in the enzymatic treatments was analyzed by HPLC (resin in $Pb^{2+}$ form). The hydrolysis yield was calculated from the detected monomeric carbohydrates. The results with various xylanase enzymes and various dosages are shown in Table IX below.

TABLE IX

| Xylanase product | Dosages of enzyme activities per g of sample DS | | | Xylose yield, % on sample DS | |
|---|---|---|---|---|---|
| | xylanase IU | beta-xylosidase nkat | acetyl esterase nkat | 22 h | 45 h |
| Irgazyme 40-4x | 12500 | 230 | 560 | 84 | 88 |
| Multifect EP809 | 2300 | 960 | 300 | 86 | 91 |
| Multifect EP809 | 570 | 240 | 77 | 62 | 75 |
| Multifect mixture | 1700 | 64 | 64 | 58 | 73 |

The results of Table IX show that the aspen xylan was hydrolyzed to xylose by xylanase enzymes with different activity profiles. The maximum xylose yield obtained was 91% on dry solids of the xylan sample. Xylose can be recovered after hydrolysis from the filtered hydrolysis solution, e.g. by a conventional crystallization procedure.

EXAMPLE 21

A paper-grade pulp sample and a dissolving-grade pulp sample both produced by a sulfite method (Rauma Ltd) were treated with xylanase enzyme to produce degraded xylan to be used as a xylose raw material. For the enzymatic treatment of wet pulp, samples were slurried into water to the concentration of 40 g DS/l and 13 kg of the slurry was exposed to the xylanase treatment in the following conditions:

| | |
|---|---|
| temperature | 50° C. |
| pH | pH 5 |
| incubation time | 2 h |
| agitation | 80 rpm |

After the incubation the degraded xylan was recovered from the filtrate of the pulp suspension. The amount of degraded xylan was determined as xylose (HPLC, ion exchange resin in $Pb^{2+}$ form) after the acid hydrolysis. The results with two enzyme dosages are shown in Table X below.

TABLE X

| | Paper-grade pulp | Dissolving-grade pulp |
|---|---|---|
| alfa-cellulose | 87% | 91% |
| Multifect EP 809* dosage xylanase IU/g D.S. | Dissolved xylan as xylose, % on pulp D.S. | |
| 10 IU | 1.25 | 0.1 |
| 30 IU | 2.5 | 0.4 |

*Genencor Int.

What is claimed is:
1. A process for producing crystalline xylose from xylan which is extracted from a paper-grade hardwood pulp containing 15 to 20 weight percent xylan calculated on the pulp during conversion of the paper-grade hardwood pulp to dissolving-grade pulp comprising the steps of:

(a) extracting said paper-grade hardwood pulp with an alkali or enzyme to obtain more than 10 weight percent of extracted xylan calculated on the paper-grade hardwood pulp;

(b) recovering said extracted xylan containing more than 90 weight percent of xylan calculated on the carbohydrates of said extracted xylan;

(c) subjecting said extracted xylan to acid hydrolysis or enzymatic hydrolysis to convert said xylan to xylose;

(d) subjecting the xylose to supersaturation conditions sufficient to crystallize the xylose; and (e) recovering the crystallized xylose.

2. The process of claim 1 further comprising the step of enriching the xylose formed in step (c), prior to performing step (d), wherein said enriching comprises a chromatographic separation process that is capable of forming an enriched xylose solution.

3. The process of claim 2 wherein the chromatographic separation process is performed in a column filled with a cationic exchanger.

4. The process of claim 1 wherein the extracting is performed using an alkaline solution as the alkali.

5. The process of claim 4 wherein the extracting is performed using sodium hydroxide.

6. The process of claim 1 wherein the acid hydrolysis is performed using sulfuric acid.

7. The process of claim 6 wherein the sulfuric acid forms sulfate ions which are removed from said xylose as precipitated calcium sulfate.

8. The process of claim 1 wherein the enzymatic hydrolysis is performed using xylanase enzymes.

* * * * *